United States Patent
Ishii et al.

(10) Patent No.: US 7,514,581 B2
(45) Date of Patent: *Apr. 7, 2009

(54) METHOD FOR PURIFYING AND PRODUCING ACRYLIC ACID

(75) Inventors: Yoshitake Ishii, Himeji (JP); Koji Ueno, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/655,112

(22) Filed: Jan. 19, 2007

(65) Prior Publication Data

US 2007/0173666 A1    Jul. 26, 2007

(30) Foreign Application Priority Data

Jan. 20, 2006    (JP) .............................. 2006-013206

(51) Int. Cl.
*C07C 51/42*    (2006.01)
*C07C 57/02*    (2006.01)

(52) U.S. Cl. ...................................... 562/600; 562/598
(58) Field of Classification Search .................. None
See application file for complete search history.

(56) References Cited

U.S. PATENT DOCUMENTS

| | | | |
|---|---|---|---|
| 5,817,865 A | 10/1998 | Machhammer et al. | |
| 5,872,288 A | 2/1999 | Haramaki et al. | |
| 7,129,376 B2 | 10/2006 | Hammon et al. | |
| 2003/0060661 A1 * | 3/2003 | Eck et al. | 562/600 |
| 2004/0116741 A1 * | 6/2004 | Nordhoff et al. | 562/600 |
| 2004/0133015 A1 | 7/2004 | Hammon et al. | |
| 2004/0147763 A1 | 7/2004 | Hammon et al. | |

FOREIGN PATENT DOCUMENTS

| | | |
|---|---|---|
| EP | 0 847 978 A1 | 6/1998 |
| EP | 1 097 741 | 5/2001 |
| JP | 9-227445 | 9/1997 |
| JP | 2001-129388 | 5/2001 |
| JP | 2004-528370 | 9/2004 |
| JP | 2004-528371 | 9/2004 |
| JP | 2005-15478 | 1/2005 |
| WO | 02/090299 A2 | 11/2002 |

* cited by examiner

*Primary Examiner*—Daniel M Sullivan
*Assistant Examiner*—Yevegeny Valenrod
(74) *Attorney, Agent, or Firm*—Wenderoth, Lind & Ponack, L.L.P.

(57) ABSTRACT

The objective of the present invention is to provide methods of efficiently purifying and producing acrylic acid by removing solid acrylic acid polymers dissolving and existing in crude acrylic acid supplied to purifying process. The purifying method of the present invention comprises: filtrating the crude acrylic acid to obtain a filtrate at temperature from 15 to 70° C. and at liquid linear velocity of 5 m/s or less, wherein the crude acrylic acid contains an acrylic acid of 50% by mass or more; and purifying the acrylic acid from the filtrate. The producing method of the present invention comprises carrying out the purifying method.

2 Claims, No Drawings

METHOD FOR PURIFYING AND PRODUCING ACRYLIC ACID

TECHNICAL FIELD

The present invention relates to a method for purifying and producing acrylic acid.

BACKGROUND ART

Acrylic acid is a useful compound because polymers and copolymers thereof are used for high water-absorbing materials, paints, adhesives, fibers, and the like. When acrylic acid is produced, though polymerization inhibitor is used since acrylic acid has a high polymerizable property, acrylic acid polymer is still formed. When the polymer exists in acrylic acid, it seems that acrylic acid tends to polymerize more easily. Further, when acrylic acid polymer accumulates, the interruption of the process might be caused by blocking the producing line with the polymers. Moreover, the polymer influences the purity of acrylic acid after purification, and it will be necessary to repeat the purifying operation many times. Accordingly, in order to carry out the efficient purification and consequently the production of acrylic acid, it is needed to exclude acrylic acid polymers in crude acrylic acid as much as possible.

As a method of excluding acrylic acid polymers formed in a process of producing acrylic acid, the method described in Japanese Unexamined Patent Publication No. 2001-129388 can be exemplified. In the publication, such a process is proposed that, in order to exclude solid impurities such as acrylic acid polymers, a processed fluid in a processing column such as a distillation column and a fractionating column is extracted once, filtered with a strainer and the like, and returned again to the processing column. However, polymer cannot be completely removed by such a usual filtrating procedure, since the temperature of the processed fluid is high and low polymerized acrylic acid polymer is dissolved in the processed fluid. Therefore, polymer which could not be removed by a usual filtrating procedure is separated out to develop problems such that the precipitation adheres on devices and causes dirt.

As a method of removing the polymers in crude acrylic acid supplied to purifying process, methods described in Published Japanese Translation of PCT International Publication Nos. 2004-528370 and 2004-528371 can be exemplified. In the publications, adhesive polymers not high in molecular weight are removed by filtering crude acrylic acid melt with a filter. However, since the operation temperature in a condensation process and an absorption process are usually high, the polymers are dissolved in crude acrylic acid. As a result, the polymers existing in crude acrylic acid cannot be completely removed by the aforementioned methods.

DISCLOSURE OF THE INVENTION

Considering the above-mentioned circumstances, the problems to be solved by the present invention are to provide methods of efficiently purifying and producing acrylic acid by removing acrylic acid polymer dissolving and existing in crude acrylic acid supplied to purification process.

The present inventors have diligently studied and found that acrylic acid can be efficiently purified and produced through precipitating acrylic acid polymers by controlling temperature of crude acrylic acid which contains acrylic acid polymers and is supplied to purification process, and further through effectively removing the precipitated acrylic acid polymers by controlling filtering conditions. The present inventors have completed the invention based on this knowledge.

A first method of the present invention for purifying acrylic acid from a crude acrylic acid obtained by at least one of absorbing or condensing an acrylic acid-containing gas produced by catalytic vapor phase oxidation reaction, comprises:

filtrating the crude acrylic acid to obtain a filtrate at temperature from 15 to 70° C. and at liquid linear velocity of 5 m/s or less, wherein the crude acrylic acid contains an acrylic acid of 50% by mass or more; and purifying the acrylic acid from the filtrate.

A second method of the present invention for purifying acrylic acid from a crude acrylic acid obtained by at least one of absorbing or condensing an acrylic acid-containing gas produced by catalytic vapor phase oxidation reaction, comprises:

filtrating the crude acrylic acid to obtain a first filtrate at temperature over 70° C. and at liquid linear velocity of 5 m/s or less, wherein the crude acrylic acid contains an acrylic acid of 50% by mass or more;

further filtrating the first filtrate to obtain a second filtrate at temperature from 15 to 70° C. and at liquid linear velocity of 5 m/s or less; and purifying the acrylic acid from the second filtrate.

A first method of the present invention for producing acrylic acid comprises:

producing an acrylic acid-containing gas by catalytic vapor phase oxidation reaction;

obtaining a crude acrylic acid containing an acrylic acid of 50% by mass or more by at least one of absorbing or condensing the acrylic acid-containing gas;

filtrating the crude acrylic acid to obtain a filtrate at temperature from 15 to 70° C. and at liquid linear velocity of 5 m/s or less; and purifying the acrylic acid from the filtrate.

A second method of the present invention for producing acrylic acid comprises:

producing an acrylic acid-containing gas by catalytic vapor phase oxidation reaction;

obtaining a crude acrylic acid containing an acrylic acid of 50% by mass or more by at least one of absorbing or condensing the acrylic acid-containing gas;

filtrating the crude acrylic acid to obtain a first filtrate at temperature over 70° C. and at liquid linear velocity of 5 m/s or less;

further filtrating the first filtrate to obtain a second filtrate at temperature from 15 to 70° C. and at liquid linear velocity of 5 m/s or less; and purifying the acrylic acid from the second filtrate.

DETAILED DESCRIPTION OF THE INVENTION

According to the present invention, acrylic acid polymer, which may obstruct smooth execution of purification process of acrylic acid, can be removed before purifying, and purifying and consequently producing acrylic acid can be efficiently carried out.

A method of the present invention for purifying acrylic acid from a crude acrylic acid obtained by at least one of absorbing or condensing an acrylic acid-containing gas produced by catalytic vapor phase oxidation reaction, comprises:

filtrating the crude acrylic acid to obtain a filtrate at temperature from 15 to 70° C. and at liquid linear velocity of 5 m/s or less, wherein the crude acrylic acid contains an acrylic acid of 50% by mass or more; and purifying the acrylic acid from the filtrate.

The producing method of the present invention comprises carrying out the purifying method.

In the method of the present invention, first, an acrylic acid-containing gas is produced by catalytic vapor phase oxidation reaction. The reaction is well-known to the person skilled in the art, and the person skilled in the art can produce an acrylic acid-containing gas by the reaction according to conventional method.

In the method of the present invention, a crude acrylic acid which is obtained by at least one of absorbing the acrylic acid-containing gas produced by catalytic vapor phase oxidation reaction in a solvent or condensing the acrylic acid-containing gas and contains acrylic acid at least 50% by mass or more is used. The method for obtaining the aforementioned crude acrylic acid is well-known and described in, for example, Japanese Unexamined Patent Publication No. 09-227445, No. 2005-15478, and the like.

The crude acrylic acid means a crude product obtained by condensing the acrylic acid-containing gas produced by catalytic vapor phase oxidation reaction, or acrylic acid solution obtained by absorbing the acrylic acid-containing gas produced by catalytic vapor phase oxidation reaction in a solvent, or the like.

Solvents used for absorbing the acrylic acid-containing gas include water; water containing organic acid; inert and hydrophobic organic liquids with high boiling points such as diphenyl ether, biphenyl, and the like; and these mixtures. Among these, water; and the mixed solvent of diphenyl ether and biphenyl are preferable.

In the present invention, the content of acrylic acid in the crude acrylic acid is 50% by mass or more, preferably 60% by mass or more, and more preferably 70% by mass or more.

Components other than acrylic acid in the crude acrylic acid include by-products of catalytic vapor phase oxidation reaction, such as water, acetic acid, maleic acid, aldehydes, acrylic acid polymers, and the like, and solvents absorbing the above-mentioned acrylic acid-containing gas, and the like.

The crude acrylic acid may contain a polymerization inhibitor, a stabilizer, and the like. The acrylic acid polymer is still formed even if a polymerization inhibitor, a stabilizer, and the like are contained.

The crude acrylic acid obtained by catalytic vapor phase oxidation reaction possibly contains acrolein as aldehydes. The acrolein is an intermediate generated from a material gas such as propylene by catalytic vapor phase oxidation reaction or a material of acrylic acid. The crude acrylic acid may be supplied to an acrolein separation column to remove the acrolein.

An exchanging frequency of filter in the filtrating process thereafter can be further decreased by reducing an amount of the acrolein of the crude acrylic acid.

The kind of the acrolein separation column is not particularly restricted as long as acrolein can be removed. The acrolein separation column is exemplified by a packed column, a plate column, i.e. tray column, or the like. It is possible in the acrolein separation column to appropriately select a purifying method such as distillation or stripping according to the concentration of acrylic acid or acrolein in the crude acrylic acid or the like.

In case that distillation is carried out in the acrolein separation column, it is preferable to set a column top pressure in the range of 20 to 800 hPa, more preferably 40 to 600 hPa, further more preferably 60 to 400 hPa, by absolute pressure. If the absolute pressure falls less than 20 hPa, it might be necessary in some cases that the devices such as the column, a condenser and vacuum device should be enlarged. As a result, the cost of equipments is increased. On the other hand, if the absolute pressure exceeds 800 hPa, polymer could generate by rising temperature in the separation column in some cases.

The condition for carrying out stripping in the acrolein separation column is also well-known to the person skilled in the art. The person skilled in the art can remove acrolein by stripping in a general condition.

Though the filtrating operation described as follows is carried out before purifying operation, "before purifying operation" in the present invention means before purifying of either of times when the purifying operation is repeatedly carried out, such as before the second purifying operation, and before the third purifying operation.

That is, in the present invention, when the purifying operation is repeatedly carried out, the filtrating operation may be carried out before the purifying operation of either of times, or the filtrating operation may be carried out before each purifying operations. For example, filtrating the crude acrylic acid, which is obtained by absorbing the acrylic acid-containing gas produced by catalytic vapor phase oxidation reaction in a solvent and/or condensing the acrylic acid-containing gas and contains acrylic acid of at least 50% by mass or more, before the first purifying operation is a first embodiment. The embodiment is preferable for the present invention. Moreover, an embodiment, in which the crude acrylic acid is once purified without filtrating operation and filtrated the once purified crude acrylic acid before second purifying operation, is also included in the scope of the present invention.

Before being supplied to the filtrating operation, the crude acrylic acid is cooled to 15 to 70° C., and preferably to 15 to 50° C. Though the crude acrylic acid usually contains 1000 ppm by mass or less of the dissolved acrylic acid polymers, since the solubility of the acrylic acid polymers in the aqueous crude acrylic acid solution changes rapidly at around 70° C., the crude acrylic acid is cooled to 70° C. or less in order to precipitate the acrylic acid polymers sufficiently. On practical use, the acrylic acid polymers are precipitated enough by carrying out the filtrating operation while cooling the polymer to 65° C. or less, or 60° C. or less, or to 55° C. or less if circumstances require, and then the precipitated polymers are separated by filtration. On the other hand, since the melting point of acrylic acid is about 13° C., the temperature for the filtrating operation is to be 15° C. or more from the viewpoint of preventing the crystal precipitation of acrylic acid.

Though a well-known technology may be adopted properly to cool the crude acrylic acid of the present invention, it is preferable to cool the crude acrylic acid with a heat exchanger. The cooling efficiency with the heat exchanger is good, and the device is cheap and can be miniaturized, and it is also easy to handle the device. The type of the heat exchanger is not especially limited, and examples thereof include the plate type, the spiral type, the double-pipe type, the shell-and-tube type, and the like. In the present invention, a pre-filter may be further installed in front of the heat exchanger to prevent solids such as dust being blocked in the heat exchanger part. The material and the filter diameter of the pre-filter are not especially limited, and an automatic strainer may be used as the pre-filter. Cooling by heat radiation using piping and the like without using a heat exchanger is not recommended since it takes time and the productivity is comparatively bad.

The cooled crude acrylic acid is supplied for the filtrating operation. The filtrating operation is carried out at temperature from 15 to 70° C., and preferably at temperature from 15 to 50° C. in the present invention. As the aspect with the best filtration efficiency, first the filtration is carried out at temperature over 70° C. and the preferable upper limit of temperature is 100° C. or less from the viewpoint of the polymerizable property of acrylic acid, and further the filtration is carried out at temperature from 15 to 70° C. Catalyst fragments, dust and the like are removed beforehand by carrying out the filtration first at temperature over 70° C., and further the filtration is carried out also at temperature from 15 to 70° C., preferably at temperature from 15 to 50° C., to remove the precipitated acrylic acid polymers. By carrying out such a filtrating operation of two stages or more at different temperature, objective substances for the filtration can be separated and the exchange frequency of the filter can be greatly decreased. In addition, when the crude acrylic acid is cooled with a heat exchanger, blocking in the heat exchanger with solids such as dust can be prevented by carrying out the filtration at temperature over 70° C. in front of the heat exchanger.

When the filtrating operation is carried out, the linear velocity of the solution is to be 5 m/s or less. The linear velocity is preferable to be 0.0005 to 2 m/s, and more preferable to be 0.001 to 1.0 m/s. The reason is that the precipitated polymer might pass the filter when the linear velocity is over 5 m/s. The linear velocity in the present invention can be obtained by dividing the amount of the solution which passes the filter by the filtration area of the filter.

The kind of the filter is not especially limited, and filters usually used can be used. Examples thereof include a metallic basket filter knitted with stainless steel wire and the like, a nonwoven fabric, a woven cloth, a filter paper, a glass filter, a ceramic filter, and a filter made of a resin such as polypropylene. Among them, a metallic basket filter and a filter made of polypropylene are preferable from the viewpoint of acid resistance, alkali resistance, strength, cost, versatility, and operationality.

Though the diameter of the filter may have a size in which the precipitated acrylic acid polymers can be separated by filtration and is not especially limited. The diameter is preferably to be 0.01 to 1000 µm, more preferably to be 0.1 to 500 µm, and still more preferable to be 0.1 to 100 µm. When filters of two stages or more are installed, it is better to install the filters successively from the one with rough mesh to the one with fine mesh from the viewpoint of the filter lifetime. For example, the diameter of the filter of the first stage is to be 100 to 1000 µm, and more preferable to be 120 to 1000 µm, and the diameter of the second stage or later is to be 0.1 to 100 µm, more preferable to be 0.5 to 100 µm, and further preferable to be 1 to 80 µm. In this case, the raw materials of the filters of each stage may be same or different each other. In addition, when a by-pass is installed in preparation for the filter exchange, the arrangement, the composition, and the raw material of the filter in the by-pass are preferable to be the same as those in the main path.

The position where the filter is installed is not especially limited, and may be in the front of or behind a pump for sending the crude acrylic acid. Moreover, the number of filter to be installed is not especially limited, and may be one or plural. The installation of the filter may be done, for example, by the installation of an automatic strainer and the like. The automatic strainer is suitable because it is possible to scrape away extraneous matter automatically.

The crude acrylic acid to be supplied for the purifying operation may be stored in a tank once. When the crude acrylic acid is stored in a tank, the filtrating operation may be carried out before or after the storage in the tank. The filtrating operation is preferably carried out before the storage.

In addition, it is also effective in removing impurities in the crude acrylic acid to prepare a filter in front of the cooling device of the crude acrylic acid separately.

The filter causes clogging since the filter catches the acrylic acid polymers while being used. The polymers of acrylic acid can be easily removed by carrying out the back wash and/or the water washing, the alkaline washing successively. The filter can be regenerated by being washed further with water. Further, since a wash liquid obtained by the first water washing contains acrylic acid, the wash liquid may be circulated to one step of acrylic acid producing process, for example, the collection process, and the acrylic acid can be recovered.

The crude acrylic acid from the filtrating step, that is filtrate, is supplied to the purifying. The conventional purifying method such as distillation, crystallization, solvent extraction, and chromatography may be adopted as the purifying operation. Among them, distillation and crystallization are preferable from the viewpoint of the production efficiency, and the crystallization is particularly preferable.

The method for purifying described above can be directly applied to the method for producing acrylic acid, including the catalytic vapor phase oxidation reaction step, the step of obtaining a crude acrylic acid by means such as absorbing acrylic acid-containing gas in a solvent or condensing the gas, filtrating step, and purifying step. The method for producing acrylic acid is useful since acrylic acid can be efficiently produced.

EXAMPLES

In the following, though the present invention will be described by Examples and Comparative Examples, the present invention should not be limited by these Examples.

Example 1

Acrylic acid gas obtained by catalytic vapor phase oxidation reaction was collected by water to obtain a crude acrylic acid, that is an aqueous acrylic acid solution, of 90% in acrylic acid concentration. The crude acrylic acid was cooled with a heat exchanger, and then filtrating process was carried out by passing the crude acrylic acid through a metallic strainer with mesh roughness of 50 µm at the state of 65° C. in liquid temperature. The liquid linear velocity of the crude acrylic acid at the time of the filtration process was 0.01 m/s. The crude acrylic acid after completion of filtration was sent to the next process of falling liquid film crystallizer of which the pipe length is 18 m and the inside diameter is 70 mm. As for the liquid after the filtration process had been carried out, precipitation of dissolved acrylic acid polymers was a little even at the time of cooling in the crystallizating process, and no turbidity was generated in the product. When the crystallizer was checked after it had stably operated for one year, the adhesion of the extremely small amount of polymers was confirmed. However, there was no influence of the adhesion on the operation at all.

Example 2

A similar operation to Example 1 was carried out, except that the filtrating process was carried out at the state that the liquid temperature of the crude acrylic acid was 30° C. The accumulation of acrylic acid polymers in the strainer was a little much compared with that at the time of 65° C. in filtration temperature, and the exchange frequency of the strainer went up. However, as for the liquid that the filtrating process had been carried out, the precipitation amount of the dissolved acrylic acid polymers was smaller than that in Example 1 even at the time of cooling in the crystallizating process, and no turbidity was generated in the product. The accumulation of acrylic acid polymers in the strainer was a little much compared with that in Example 1, and the exchange frequency went up by about 20%. However, when the crystallizer was checked after it had stably operated for one year, no polymer was adhered at all.

Example 3

Acrylic acid gas obtained by the catalytic vapor phase oxidation reaction was collected by water to obtain crude acrylic acid, that is an aqueous acrylic acid solution, of 90% in acrylic acid concentration. The crude acrylic acid was cooled with the heat exchanger, and then the filtrating process was carried out by passing the crude acrylic acid through a metallic strainer with mesh roughness of 250 μm at the state of 90° C. in liquid temperature. Hereinafter, the filtrating process is referred to as the first stage filtration. Further the crude acrylic acid, that is the filtrate of the first stage filtration, was cooled with the heat exchanger to 30° C., and the filtration process was carried out by passing the crude acrylic acid through a metallic strainer with mesh roughness of 50 μm. Hereinafter, the filtration process is referred to as the second stage filtration. The liquid linear velocity of the crude acrylic acid at the time of the filtration process was 0.01 m/s for both stages. The crude acrylic acid which had processed the filtration was sent to the next process of falling liquid film crystallizer of which the pipe length is 18 m and the inside diameter is 70 mm. As for the liquid that the filtrating process had been carried out, the precipitation of the dissolved acrylic acid polymers was a little even at the time of cooling in the crystallizating process, and no turbidity was generated in the product. Catalyst fragments, dust, and the polymers with high polymerization degree of acrylic acid were captured by the strainer in the first stage, and the polymers with low polymerization degree of acrylic acid were captured by the strainer in the second stage. The exchange frequency of each strainer in the first stage and the second stage was lower than that in Example 1. When the crystallizer was checked after it had stably operated for one year, no polymer was adhered at all.

Example 4

A similar operation to Example 3 was carried out, except that removing procedure of acrolein was carried out between collecting process and the first filtrating procedure. In the removing procedure of acrolein, crude acrylic acid was supplied to the upper portion of an packed column of which the inside diameter is 100 mm, the height of packed part is 5 m, the column top pressure was set as 265 hPa by absolute pressure, and the temperature of the column bottom as 90° C., to remove acrolein by distillation. The gas obtained from the column top of the packed column was supplied to lower part of the collecting column of acrylic acid. The crude acrylic acid, in which the concentration of acrylic acid was 90% and the concentration of acrolein was 0.003%, was obtained from the column bottom by the removing procedure. On the other hand, the concentration of acrolein obtained from the collecting column was 0.03% in the Example 3. Accordingly, it was demonstrated that a concentration of acrolein could be adequately decreased by removing procedure of acrolein. As a result, the exchanging frequency of strainer in the first and second filtrating procedure could be decreased, compared to the case of Example 3. In addition, when the crystallizer was checked after it had stably operated for one year, no polymer was adhered at all.

Comparative Example 1

A similar operation to Example 1 was carried out, except that the filtrating process was carried out at the state that the liquid temperature of the crude acrylic acid was 75° C. The accumulation of the acrylic acid polymers was hardly found in the strainer, and the acrylic acid polymers were sent to the next process with being dissolved intact in the crude acrylic acid at 75° C. Since the removal of the acrylic acid polymers was imperfect, the acrylic acid polymers, which had been dissolved till then, were precipitated when cooled in crystallization process. The acrylic acid polymers were mixed in the product, and turbidity was generated. Moreover, since the clogging by the precipitation of the acrylic acid polymers was generated in the liquid disperser on the top part of the crystallization column, washing was needed after the operation of about one month.

Comparative Example 2

A similar operation to Example 1 was carried out, except that the filtrating process was carried out at the state that the liquid temperature of the crude acrylic acid was 10° C. Since the polymers and crystals of acrylic acid clogged the strainer and the crystals of acrylic acid precipitated also in the liquid stay part of the solution sending line, and consequently the solution sending was not steady, the operation was unavoidably stopped.

Comparative Example 3

A similar operation to Example 1 was carried out, except that the liquid linear velocity of the crude acrylic acid at the time of the filtration process was 6 m/s. The accumulation of the acrylic acid polymers in the strainer was very little compared with that when the liquid linear velocity of the crude acrylic acid was 0.01 m/s in Example 1, and though the dissolved acrylic acid polymers were precipitated, the polymers could not be caught in the straner. As a result, though the crude acrylic acid which had processed the filtration was sent to the next process of the falling liquid film crystallizer, turbidity with the acrylic acid polymers was generated in the product. Moreover, since the clogging by the precipitation of the acrylic acid polymers was generated in the liquid disperser on the top part of the crystallization column, washing was needed after the operation of about two months.

INDUSTRIAL APPLICABILITY

The present invention is useful as a method by which acrylic acid, which is the raw material of high water-absorbing materials, paints, adhesives, fibers, and the like, can be efficiently purified and produced.

The invention claimed is:

1. A method for producing acrylic acid, comprising:
   producing an acrylic acid-containing gas by catalytic vapor phase oxidation reaction;
      obtaining a crude acrylic acid containing an acrylic acid of 50% by mass or more by at least one of absorbing or condensing the acrylic acid-containing gas;
      filtrating the crude acrylic acid to obtain a first filtrate at temperature over 70° C. and at liquid linear velocity of 5 m/s or less, to remove catalyst fragments and dust;
      further filtrating the first filtrate to obtain a second filtrate at temperature from 15 to 70° C. and at liquid linear velocity of 5 m/s or less, to remove acrylic acid polymer; and
      crystallizing the acrylic acid from the second filtrate.

2. The method according to claim 1, wherein the filtrating the first filtrate is conducted at a temperature which prevents crystal precipitation of acrylic acid.

* * * * *